(12) United States Patent
Osti

(10) Patent No.: US 11,589,910 B2
(45) Date of Patent: Feb. 28, 2023

(54) TENSIONING DEVICE FOR TENDONS

(71) Applicant: Leonardo Osti, Modena (IT)

(72) Inventor: Leonardo Osti, Modena (IT)

(*) Notice: Subject to any disclaimer, the term of this patent is extended or adjusted under 35 U.S.C. 154(b) by 0 days.

(21) Appl. No.: 16/318,967

(22) PCT Filed: Jul. 19, 2017

(86) PCT No.: PCT/IB2017/054373
§ 371 (c)(1),
(2) Date: Jan. 18, 2019

(87) PCT Pub. No.: WO2018/015905
PCT Pub. Date: Jan. 25, 2018

(65) Prior Publication Data
US 2019/0298429 A1    Oct. 3, 2019

(30) Foreign Application Priority Data

Jul. 20, 2016   (IT) .......................... 102016000076352

(51) Int. Cl.
| | | |
|---|---|---|
| *A61B 17/88* | (2006.01) | |
| *A61B 90/00* | (2016.01) | |
| *A61F 2/08* | (2006.01) | |
| *A61B 17/56* | (2006.01) | |
| *A61B 17/04* | (2006.01) | |
| *A61B 5/00* | (2006.01) | |

(52) U.S. Cl.
CPC .......... *A61B 17/8869* (2013.01); *A61B 90/06* (2016.02); *A61F 2/0805* (2013.01); *A61B 5/4523* (2013.01); *A61B 5/4533* (2013.01); *A61B 2017/0496* (2013.01); *A61B 2017/564* (2013.01); *A61B 2090/064* (2016.02)

(58) Field of Classification Search
CPC ................ A61B 17/8869; A61B 17/88; A61B 2017/0496; A61B 2017/0469; A61B 2017/0483; A61B 90/06; A61B 2090/064; A61B 2017/0409; A61F 2/0805; A61F 2/0811; A61F 2002/0888
See application file for complete search history.

(56) References Cited

U.S. PATENT DOCUMENTS

| | | | | | |
|---|---|---|---|---|---|
| 4,712,542 | A | * | 12/1987 | Daniel ................ | A61F 2/0805 606/96 |
| 4,950,271 | A | * | 8/1990 | Lewis ................. | A61F 2/0805 606/102 |
| 5,071,420 | A | * | 12/1991 | Paulos ................ | A61F 2/0805 606/104 |

(Continued)

FOREIGN PATENT DOCUMENTS

| | | |
|---|---|---|
| EP | 1159925 A2 | 12/2001 |
| WO | 2009129269 A2 | 10/2009 |

*Primary Examiner* — Erich G Herbermann
*Assistant Examiner* — Brigid K Byrd
(74) *Attorney, Agent, or Firm* — David B. Tingey; Bryant J. Keller; Kirton McConkie

(57) ABSTRACT

The tensioning device for tendons comprises: a main body of elongated conformation having at one ending part a positioning portion comprising a pointer element adapted to be positioned onto a bone portion; hooking means to an injured tendon portion; measuring means operatively connected to the hooking means and adapted to detect a tension value at the bone portion.

12 Claims, 3 Drawing Sheets

(56) References Cited

U.S. PATENT DOCUMENTS

| | | | | |
|---|---|---|---|---|
| 5,370,661 | A | * | 12/1994 | Branch .............. A61B 17/0401 24/16 R |
| 5,713,897 | A | * | 2/1998 | Goble ................... A61F 2/0805 606/1 |
| 6,171,310 | B1 | | 1/2001 | Giordano et al. |
| 6,592,609 | B1 | * | 7/2003 | Bonutti .............. A61B 17/0401 606/232 |
| 6,679,889 | B1 | * | 1/2004 | West, Jr. ............... A61F 2/0805 606/327 |
| 2005/0049598 | A1 | * | 3/2005 | West ..................... A61F 2/0805 606/90 |
| 2006/0167464 | A1 | * | 7/2006 | Allen ................. A61B 17/8869 606/103 |
| 2009/0228015 | A1 | * | 9/2009 | Ellis .................... A61B 5/1076 606/87 |
| 2016/0157852 | A1 | * | 6/2016 | Dougherty ......... A61B 17/0401 606/232 |

* cited by examiner

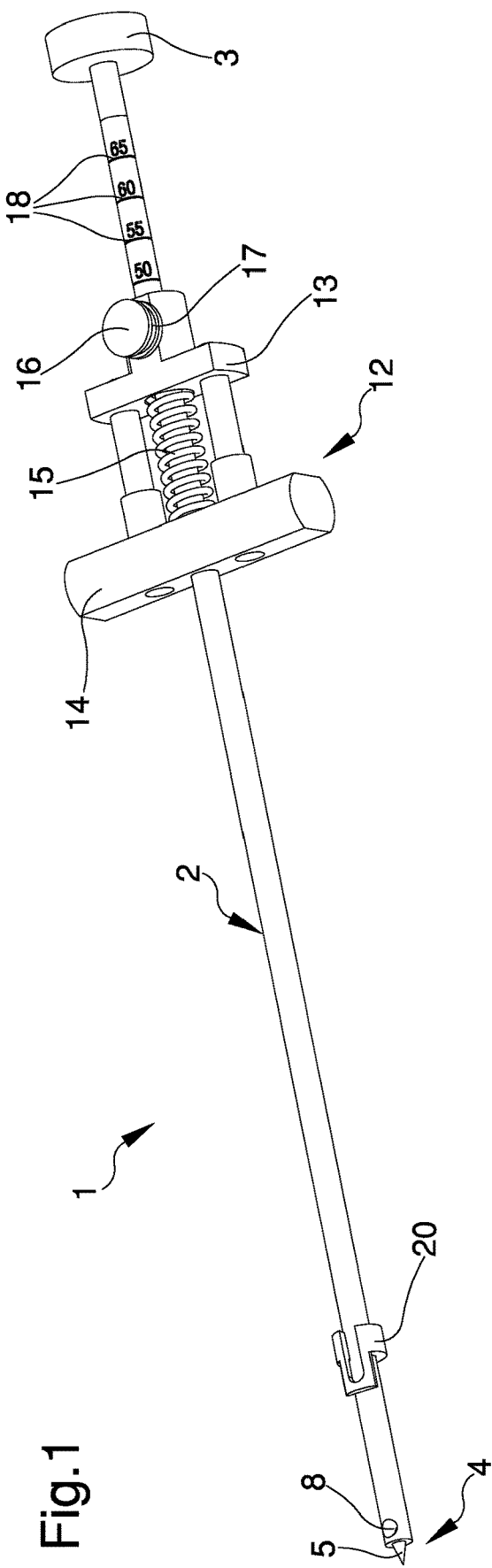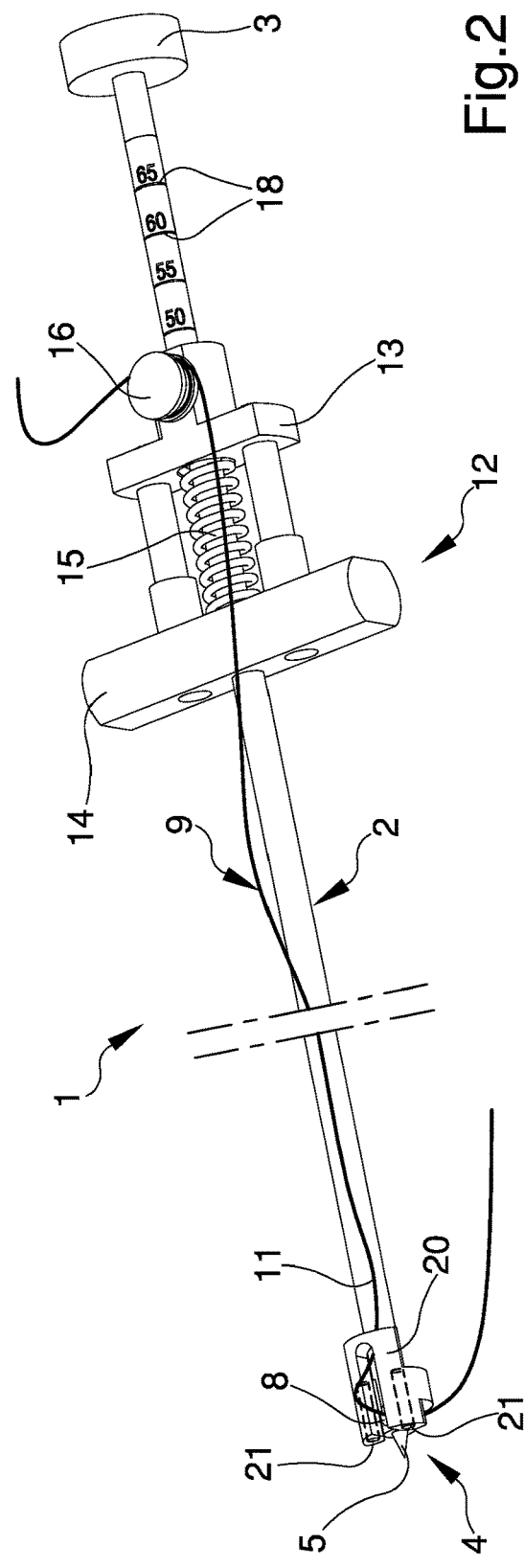

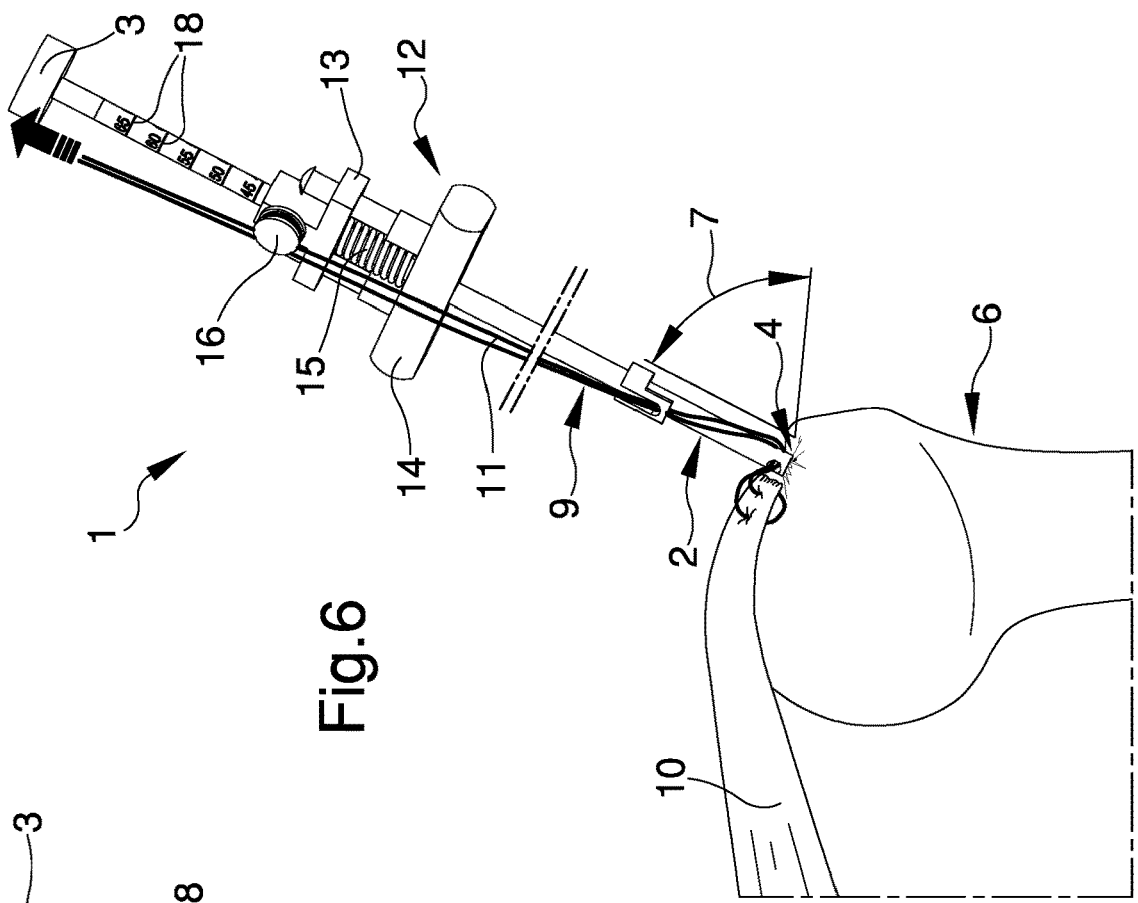
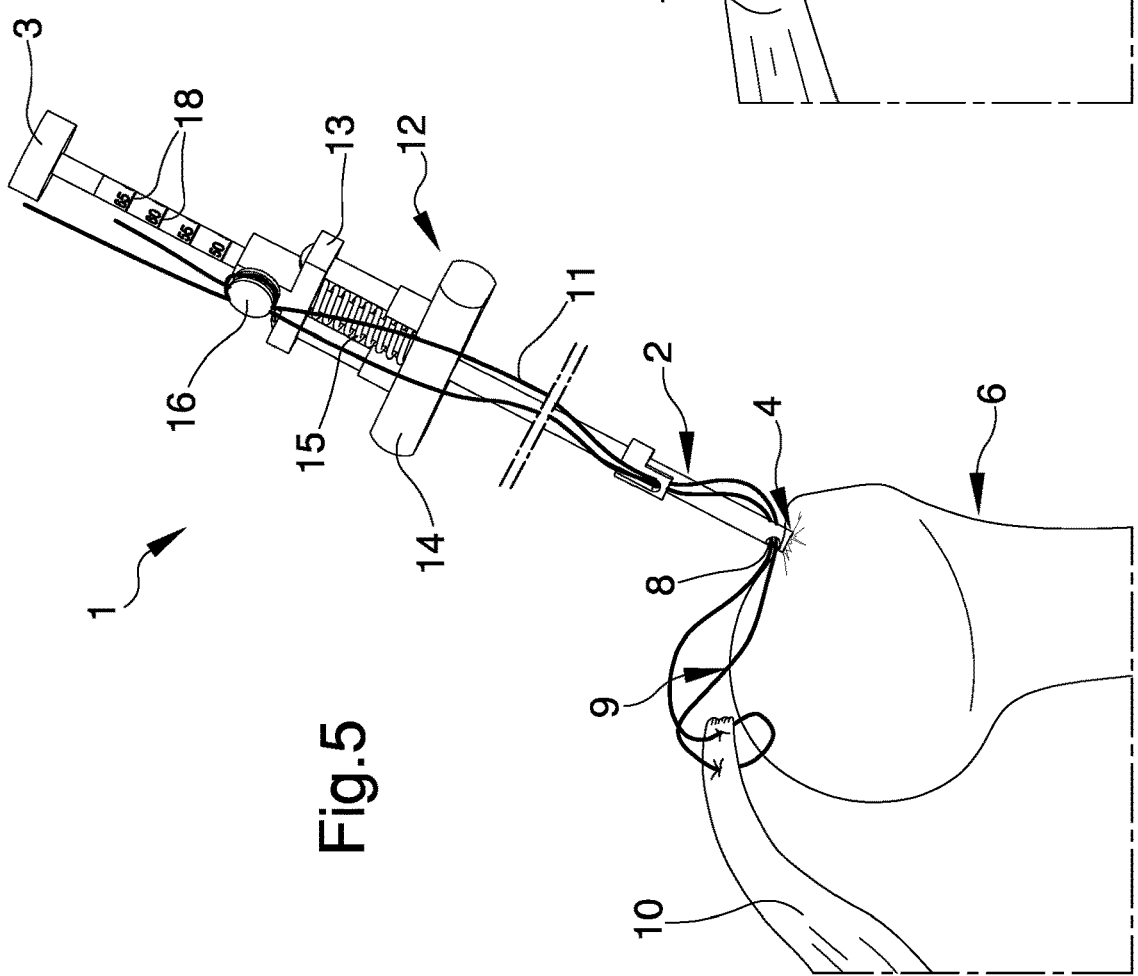

TENSIONING DEVICE FOR TENDONS

TECHNICAL FIELD

The present invention relates to a tensioning device for tendons.

BACKGROUND ART

With reference to the restoration of the function of tendons in the surgical field, it is known that tendons are a fundamental element of the human musculoskeletal apparatus, representing the link between the bone apparatus and the muscular apparatus.

The main function of the tendons is that of transmitting the force exerted by the muscles to the structures to which they are connected. In order to withstand the high stresses to which they are subjected, tendons are provided with high resistance and low elasticity.

For these reasons, in the event of severe tendon injuries involving partial or total breakage, tendons lose their functions and regress to a retracted position relative to the point in which injury has occurred.

The repair of injured tendons is achieved by tensioning and anchoring the latter to the bone by means of small size screws associated at one ending part with the injured tendon portion and inserted to measure in anchoring holes made on the bone.

In detail, the restoring procedure involves traction of the injured tendon portion from the retracted position to a restoring position arranged in the proximity of the tear point and the fixing of the injured tendon portion itself onto the bone, so as to restore the link between the bone apparatus and the muscular one.

In practice, the positioning of the injured portion is carried out by means of the association of an injured ending part with a traction element.

The traction element is of the type of a suture wire and is made to pass from side to side of the injured ending part, so as to allow it to shift from the retracted position to the restoring position wherein the tendon is stretched and subjected to traction.

To date, the traction of the injured ending part is carried out manually, and the repair tension to which the tendon is subjected once restored is measured in an empirical way.

However, repair tension values are variable depending on the biological state of the injured tendon, on the elasticity of the tendon tissue and of the muscular tissue to which the tendon is tied, on the patient's physical characteristics and on the restoring position.

In particular, the restoring position plays a fundamental role in determining the repair tension to which the tendon is subjected, in fact, with high tension values, the risk of subsequent injuries and/or breakages is extremely high.

This method has several drawbacks, among which it is worth noting the fact that these values are not comparable and hence they prevent the carrying out of studies aimed at determining the optimal repair tension to which the injured tendon portion can be restored.

In addition, the detected repair tension values are unlikely with respect to the actual tension values to which the tendon portion is subjected; this is due to the fact that the position in which the repair tension is detected does not coincide with the actual restoring position in which the tendon is associated with the bone.

An alternative solution to this method is represented by a first type of tensioning devices having a main body of elongated shape and provided at a first ending part with a grip portion, and at a second ending part with hooking means of the injured tendon portion.

Moreover, the first ending part is provided with tensioning means adapted to position the injured tendon portion at the selected restoring position.

However, even in this case, the tensioning of the injured tendon portion is carried out in an empirical way, by preventing the monitoring and collection of the tension values to which the tendon portion itself is subjected in the restoring position.

A second type of tensioning devices is described in U.S. Pat. No. 4,712,542.

Nevertheless, this device also has some drawbacks, such as the fact that, similarly to the manual repair procedure, also in this case it is not possible to detect the repair tension in a comparable manner with other tension values detected.

Further types of tensioning devices are described in patent documents EP 1 159 925, US2016/0157852, U.S. Pat. Nos. 4,712,542, 6,171,310 and WO 2009/129269. The tensioning devices described in these documents prevent different repair tension values from being measured during the restoring procedure.

In detail, none of them allows to collect different measurements depending on the placement position of the tensioning device and on the inclination taken by it with respect to the bone portion.

For example, EP1159925 describes a tensioning device provided with a first main body and a second main body, in which one of them performs the function of a support element for the other main body which is adapted to tension the injured portion.

In other words, one of the two main bodies abuts the bone portion performing the function of a resting point for the tensioning of the injured portion which, on the other hand, is made by means of the second main body.

It is easy to understand that the fact of providing two main bodies greatly complicates the restoring operations, which is added to the fact that in case of hardly reachable injured portions and devoid of resting points, the aforementioned device proves to be unusable.

Additionally, it does not allow the measurement and collection of different tension values, but simply the positioning of the injured portion in the restoring position.

Similarly, also the remaining patent documents have substantially the same drawbacks, in particular as regards the collection of tension values, their reproducibility with values similar to those to which the tendon is subjected in the restoring position, i.e. anchored to the bone portion and, finally, the lack of a stable anchoring point of the tensioning device to the bone portion.

Another type of tensioning device, known under the trade name "KT1000", can be used to quantify the ligament stability in an objective way, in the present case the anterior cruciate ligament of the knee, as a result of a traumatic event.

This device is placed resting on the knee and, by means of the application of progressively increasing forces, the tendon stability values detected are measured.

Even in this case, it is not possible to detect the repair tension to which the restored tendon portion is subjected, but only the laxity values of the tendon tissue.

At the same time, in the surgical field the need is felt to speed up the healing process of the tendon injury, in order to reduce the recovery time of the patient.

DESCRIPTION OF THE INVENTION

The main aim of the present invention is to provide a tensioning device for tendons that allows measuring in an objective way the repair tension to which the restored tendon is subjected.

Another object of the present invention is to provide a tensioning device for tendons which allows carrying out repeatable and comparable measurements, thus obtaining repair tension values which are likely to those actually exerted on the injured and restored tendon portion.

Another object of the present invention is to provide a tensioning device for tendons, which allows to overcome the mentioned drawbacks of the prior art within the ambit of a simple, rational, easy, effective to use and low cost solution.

The above mentioned objects are achieved by the present tensioning device for tendons, having the characteristics of claim 1.

BRIEF DESCRIPTION OF THE DRAWINGS

Other characteristics and advantages of the present invention will become more evident from the description of a preferred, but not exclusive, embodiment of a tensioning device for tendons, illustrated by way of an indicative, but non-limiting example in the accompanying drawings, wherein:

FIG. 1 is an axonometric view of the device according to the invention in a first embodiment;

FIG. 2 is an axonometric view of the device according to the invention in a second embodiment;

FIG. 5 is a schematic representation of the device according to the invention in a third operating configuration;

FIG. 6 is a schematic representation of the device according to the invention in a fourth operating configuration.

EMBODIMENTS OF THE INVENTION

Figure 3:
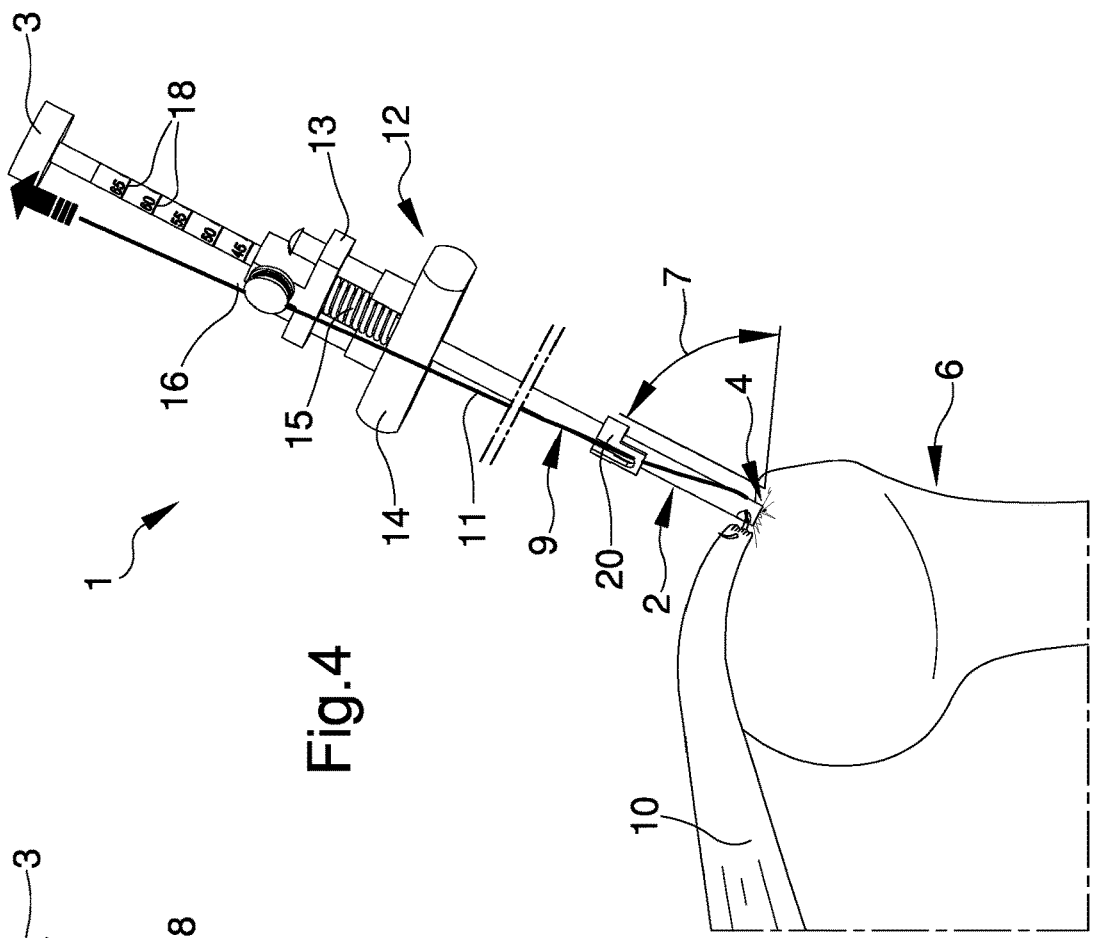
FIG. 3 is a schematic representation of the device of FIG. 2 in a first operating configuration.

With particular reference to these illustrations, globally indicated with reference numeral 1 is a tensioning device for tendons.

The device 1 comprises a main body 2 of elongated shape, having a grip portion 3 defined at one ending part of the main body 2, and at least a positioning portion 4 associated with a second ending part of the main body itself opposite to the first ending part and having a pointer element 5 adapted to be positioned onto a bone portion 6, such as e.g. the knee or the shoulder.

The main body 2 has a substantially tubular shape.

Preferably, the main body 2 has a circular cross section with a diameter of less than 8 mm.

With reference to a preferred embodiment, the main body 2 has a length of about 15 cm.

Alternative embodiments cannot also be ruled out wherein the main body 2 has a length greater than or less than the aforementioned value.

In addition, the grip portion 3 has a handle portion which, in a first embodiment shown in the figures, has a substantially discoid shape and is transversely associated with the main body 2.

Alternative embodiments cannot however be ruled out wherein the grip portion 3 has an annular shape; this means that the latter has a through hole adapted to accommodate at least one finger of an operator.

Advantageously, the pointer element 5 has a predefined inclination with respect to the bone portion 6; this means that the pointer element 5 defines with the bone portion 6 an angle 7 the extension of which is variable depending on the specific clinical needs.

In other words, the aforementioned angle 7 may vary depending on the physical characteristics of the patient and on the biological state of the injured tendon. With reference to the particular embodiment shown in the figures, the pointer element 5 has a substantially conical shape with the base associated with the positioning portion 4 and the vertex facing towards the bone portion 6.

Preferably, the pointer element 5 has a substantially pointed shape adapted to perforate the bone portion 6 in a restoring position described in detail in the following discussion.

In other words, the fact that the pointer element 5 is inserted into the bone portion 6 allows to adjust the inclination of the main body 2 with respect to the bone portion itself without varying the position of the device 1, i.e. without pulling the pointer element 5 out of the bone portion 6 and insert it again by perforating the same in another position and/or with another inclination.

In addition, the main body 2 has a through hole 8 made in the vicinity of the pointer element 5.

The hole 8 is made on top of the pointer element 5.

The device 1 comprises hooking means 9 to at least one injured tendon portion 10.

Preferably, the hooking means 9 comprise a traction element 11 passing through the hole 8 and adapted to engage with measuring means 12.

The traction element 11 is the type of a suture wire. Alternative embodiments cannot also be ruled out wherein the traction element 11 is of a different type, e.g. of the type of a flexible element having a ribbon shape.

Figure 4:
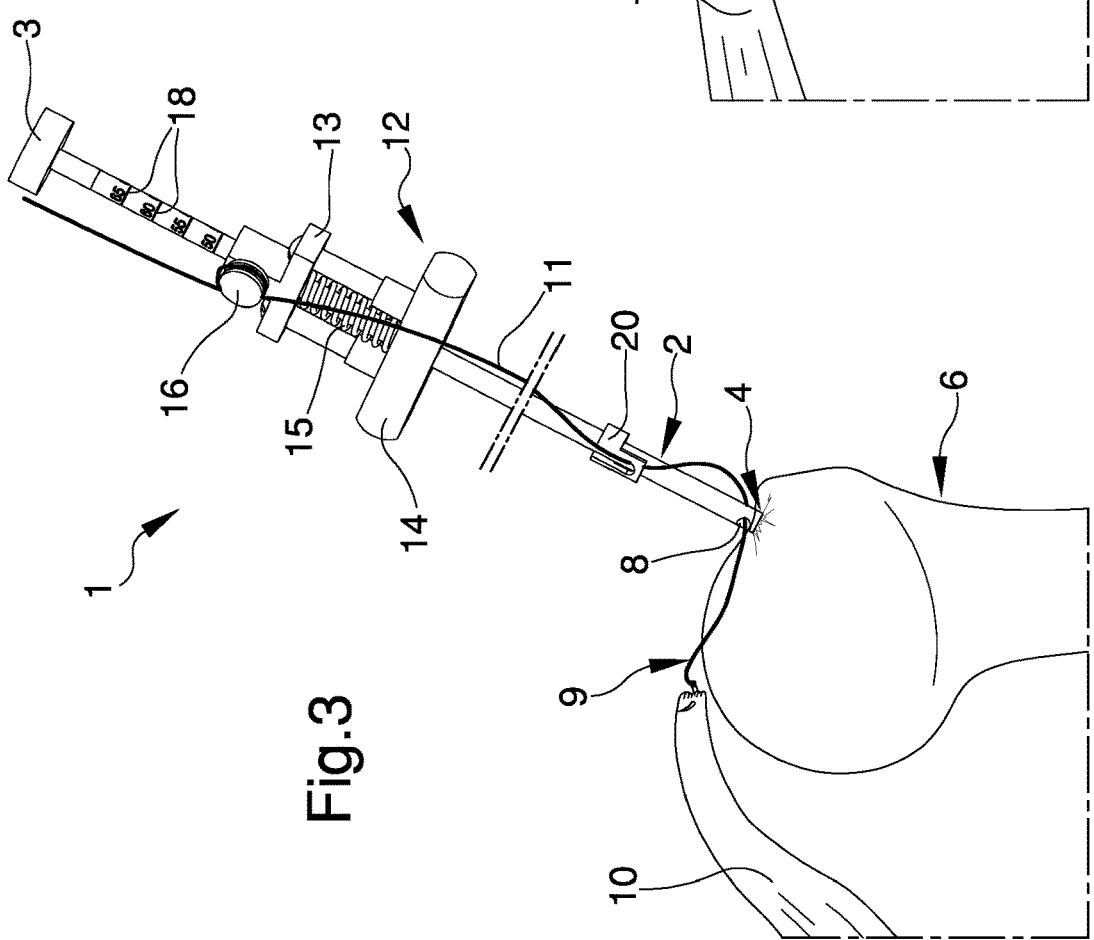
FIG. 4 is a schematic representation of the device of FIG. 2 in a second operating configuration.

In this case, the traction element 11 is associable with the injured tendon portion 10 for the shift of the same from the retracted position (FIG. 3) to the restoring position (FIG. 4).

With reference to the particular embodiment shown in FIGS. 3 and 4, the traction element 11 is associated with the tendon portion 10 by interposition of a suture needle.

At the same time, with reference to the embodiment shown in FIGS. 5 and 6, the traction element 11 passing through the tendon portion 10 forms a gripping handle with the latter; this makes it possible to significantly reduce the so-called "cheese-wire effect".

It is worth specifying that within the scope of this discussion, the term "retracted position" means the position reached by the tendon portion 10 which has been injured following the breakage thereof.

At the same time, with the term "restoring position" is meant the position of the tendon portion 10 reached as a result of the shift of the latter from the retracted position and defining the insertion point of the tendon into the bone portion 6.

In this regard it is worth specifying that the measuring means 12 are operatively connected to the hooking means 9 and are adapted to detect a tension value at the bone portion 6.

The measuring means 12 measure the tension value at the pointer element 5; in the present case, the position of the pointer element 5 is coincident with the restoring position (FIG. 4).

With reference to the particular embodiment shown in the figures, the measuring means 12 are of the type of a spring dynamometer.

In the present case, the spring dynamometer 12 is of the type known to the field technician and comprises a first plate element 13 and a second plate element 14 associated with each other by interposition of elastic means 15 of the type of a spring element.

By means of the application of force onto the plate elements 13, 14, the deformation of the spring element 15 is produced and, at the same time, the tension of the injured tendon portion 10 which is moved from the retracted position to the restoring position.

The deformation of the spring element 15 is directly proportional to the applied force and, consequently, to the tension suffered by the tendon portion 10 in the restoring position.

Furthermore, the measuring means 12 comprise a washer element 16 having a groove 17 with a substantially annular shape and adapted to accommodate the traction element 11.

With reference to the particular embodiment shown in the figures, the washer element 16 is associated with the first plate element 13.

The washer element 16 is placed on one of the plate elements 13, 14 and is adapted to maintain the traction element 11 in traction.

The measuring means 12 comprise a plurality of notch elements 18 formed on the main body 2 and corresponding to the tension values detected on the bone portion 6.

As can be seen in the figures, the notch elements 18 have a predefined reciprocal distance corresponding to specific tension values; however, the aforementioned reciprocal distance is variable depending on the physical characteristics of the patients and on the accuracy required for detecting the measured tension values.

Alternative embodiments cannot however be ruled out wherein the measuring means 12 are of the type of an electronic or piston type device.

The device 1 comprises a support element 20 adapted to direct the traction element 11.

The support element 20 comprises at least one through slot 21 in which an auxiliary surgical element of the type of a perforating element can be inserted, not shown in detail in the figures.

With reference to the particular embodiment of FIG. 2, the support element 20 comprises two through slots 21 arranged on opposite portions of the support element 20.

Finally, prior to the detailed description of the operation of the present invention, it should be specified that the fact of providing a single main body 2 anchored to the bone portion 6 by perforation allows to vary the inclination of the main body 2 with respect to the latter, and also to measure and collect the tension values of the tendon portion 10 exactly in the restoring position.

The combination of the aforementioned characteristics results in completely different technical effects to those described in patent documents EP 1 159 925, US2016/0157852, U.S. Pat. Nos. 4,712,542, 6,171,310 and WO 2009/129269.

Specifically, none of the aforementioned documents allows the measurement of the tension values and, specifically, in the exact restoring position.

Furthermore, none of the aforementioned documents allows either to measure or to vary the inclination of the device 1 with respect to the bone portion 6 to which it is anchored.

The operation of the present invention is as follows.

The device 1 is positioned on the bone portion 6, such as the knee or shoulder, affected by tendon injury.

The tendon portion 10 is in the retracted position (FIG. 3) and is hooked at one ending part by means of the traction element 11.

The pointer element 5 is anchored to the bone portion 6, by perforation of the latter, with a predefined inclination defining the angle 7.

It should be specified that the fact of anchoring the pointer element 5 to the bone portion 6 allows the reproducibility of the angle made by the tendon portion 10 in the restoring position and, therefore, the measurement of the actual tension values to which the latter is subjected.

In other words, the predefined inclination 7 of the pointer element 5 together with that of the main body 2, allows defining the angle 7, i.e. the actual inclination carried out by the tendon portion 10 in the restoring position.

The traction element 11, passing through the hole 8, is positioned in traction accommodating it within the groove 17 of the washer element 16.

At this point, by applying a force on the spring dynamometer 12, i.e. by grasping the plate elements 13, 14 and applying a compression force on the spring element 15, the traction of the tendon portion 10 is obtained; this causes the shift of the tendon portion itself from the retracted position to the restoring position.

The tension values exerted by the force applied to the dynamometer are readable by means of the notch elements 18.

In the case in which the tension values detected are excessively high, the pointer element 5 is shifted and positioned on a different portion to the bone portion 6, having lower tension values than those measured.

It has in practice been found that the disclosed invention achieves the intended objects.

In particular, it is emphasized that the particular solution of providing a tensioning device equipped with measuring means allows measuring the tendon restored tension.

In addition, the presence of measuring means associated with the traction element allows measuring in an objective way the repair tension to which the restored tendon is subjected, making repeatable and comparable measurements. Additionally, the fact of providing a pointer element allows measuring the tension exerted by the tendon in the restoring position at the point where the tendon itself is associated again with the bone portion.

In other words, the fact that the pointer element perforates the bone portion at the restoring position allows measuring the tension values accurately and precisely, without the risk of accidental shifts.

In addition, the fact of providing a stable and solid anchoring point with the bone portion allows carrying out multiple test procedures by collecting data both reproducing the actual tension values to which the tendon is subjected in the restoring position, and comparable together in order to greatly reduce the variability between these.

Furthermore, the presence of measuring means allows collecting the tension measurements during the tests performed to find the restoring position, i.e. the shifts of the pointer element onto the bone portion, allowing the verification of the tension values exerted on the injured tendon portion in the restoring position itself.

The invention claimed is:
1. A tensioning device for tendons, wherein the tensioning device for tendons comprises:
a main body of elongated conformation having at a first ending part a positioning portion comprising at least a pointer element adapted to be positioned onto a bone portion, the main body having a through hole that is disposed on top of and immediately adjacent to said pointer element, wherein the main body further comprises a grip portion disposed at a second ending part of the main body and having a handle portion, opposite to the first ending part, the main body having a predefined inclination during use with respect to said bone portion;

a hooking means that is configured to attach to an injured tendon portion so as to shift said injured tendon portion from a retracted position in which said injured tendon portion is retracted, to a restoring position in which said injured tendon portion is stretched, wherein a position of said pointer element is configured to be coincident with said restoring position; and a measuring means that is coupled to the main body and that is configured to measure a tension value at said pointer element, wherein the measuring means is operatively connected to said hooking means and adapted to detect the tension value at said bone portion, wherein said hooking means comprise a traction element that couples to said measuring means, extends along a length of a portion of said main body, and passes through said hole such that said traction element is associable with said injured tendon portion for the shift of the injured tendon portion from said retracted position to said restoring position, and wherein the main body extends through a portion of the measuring means.

2. The device according to claim 1, wherein said pointer element is shaped to provide predefined inclination with respect to said bone portion.

3. The device according to claim 1, wherein said pointer element has a substantially pointed shape adapted to perforate said bone portion in relation to said restoring position of the injured tendon portion.

4. The device according to claim 1, wherein said measuring means comprise a type of a spring dynamometer.

5. The device according to claim 1, wherein said measuring means comprise a type of an electronic device.

6. The device according to claim 1, wherein said measuring means comprise a piston type measuring device.

7. The device according to claim 1, wherein said measuring means comprise a plurality of notch elements formed on said main body and corresponding to said tension value detected on said bone portion.

8. The device according to claim 1, wherein said measuring means comprise at least a washer element having a groove with a substantially annular shape and adapted to accommodate said traction element.

9. The device according to claim 1, wherein said main body comprises only one of the pointer element at the first ending part of the main body.

10. A tensioning device for tendons, wherein the tensioning device for tendons comprises:

a main body of elongated conformation having: at a first ending part of the main body a positioning portion comprising only a single pointer element adapted to be positioned onto a bone portion, at a second ending part of the main body, opposite to the first ending part, a grip portion having a handle portion, and a through hole in the main body that is made in a vicinity of said pointer element, said main body having a predefined inclination with respect to said bone portion during use;

a hooking means that is configured to attach to an injured tendon portion so as to shift said injured tendon portion from a retracted position in which said injured tendon portion is retracted, to a restoring position in which said injured tendon portion is stretched, wherein a position of said pointer element is configured to be coincident with said restoring position; and measuring means that is connected to the main body and that is configured to measure a tension value at said pointer element, wherein the measuring means is operatively connected to said hooking means and adapted to detect the tension value at said bone portion, wherein said hooking means comprise a traction element that couples to said measuring means, extends along a length of a portion of said main body, and passes through said hole such that said traction element is associable with said injured tendon portion for the shift of the injured tendon portion from said retracted position to said restoring position, and wherein the main body extends through a portion of the measuring means and a portion of the measuring means is configured to move with respect to the main body.

11. The device according to claim 10, wherein said through hole is disposed at a side of and immediately adjacent to said pointer element.

12. The device according to claim 10, wherein said through hole is disposed immediately adjacent to said pointer element.

* * * * *